(12) United States Patent
Ritchie

(10) Patent No.: US 9,897,578 B2
(45) Date of Patent: Feb. 20, 2018

(54) CHROMATOGRAPHY COLUMNS

(71) Applicant: THERMO ELECTRON MANUFACTURING LIMITED, Altrincham (GB)

(72) Inventor: Harald Ritchie, Chester (GB)

(73) Assignee: Thermo Electron Manufacturing Limited, Cambridge (GB)

( * ) Notice: Subject to any disclaimer, the term of this patent is extended or adjusted under 35 U.S.C. 154(b) by 51 days.

(21) Appl. No.: 14/428,944

(22) PCT Filed: Sep. 19, 2013

(86) PCT No.: PCT/EP2013/069459
§ 371 (c)(1),
(2) Date: Mar. 17, 2015

(87) PCT Pub. No.: WO2014/044746
PCT Pub. Date: Mar. 27, 2014

(65) Prior Publication Data
US 2015/0219604 A1    Aug. 6, 2015

(30) Foreign Application Priority Data

Sep. 24, 2012 (GB) .................................. 1216984.3
Sep. 24, 2012 (GB) .................................. 1216985.0

(51) Int. Cl.
*G01N 30/60* (2006.01)
*B01D 15/20* (2006.01)
(Continued)

(52) U.S. Cl.
CPC ............. *G01N 30/60* (2013.01); *B01D 15/20* (2013.01); *B01J 20/103* (2013.01); *B01J 20/283* (2013.01);
(Continued)

(58) Field of Classification Search
CPC .......... G01N 30/6039; G01N 30/6069; G01N 2030/521; G01N 2030/525;
(Continued)

(56) References Cited

U.S. PATENT DOCUMENTS 4,166,102 A   8/1979 Johnson
4,732,687 A   3/1988 Muller et al.
(Continued)

FOREIGN PATENT DOCUMENTS

CN    102470286 A    5/2012
GB    1248105        9/1971
(Continued)

OTHER PUBLICATIONS

Fekete et al., "Characterization of new types of stationary phases for fast liquid chromatographic applications," Journal of Pharmaceutical and Biomedical Analysis, 50:703-709, 2009.
(Continued)

*Primary Examiner* — Paul West

(57) ABSTRACT

A chromatography column (2) containing a bed of packed particles (22, 24, 26, 28, 30), wherein the packed particles comprise fused core particles and the particle diameters of the packed particles vary along the column. Preferably, the particles (2, 24, 26, 28, 30) are arranged according to their average particle diameter, in order of increasing average particle diameter from the inlet end (4) to the outlet end (6). The bed may comprise a plurality of bed sections and each bed section has an average particle diameter calculated from the particles in that section and there are at least two different average particle diameter bed sections, wherein the particles of each bed are separated from particles of an adjacent bed by a partition that is liquid permeable to allow
(Continued)

through a flow of mobile phase. A high column efficiency can be provided with lower pressure drop per unit length of the column.

21 Claims, 5 Drawing Sheets

(51) Int. Cl.
*G01N 30/52* (2006.01)
*B01J 20/28* (2006.01)
*B01J 20/283* (2006.01)
*B01J 20/10* (2006.01)

(52) U.S. Cl.
CPC ... *B01J 20/28004* (2013.01); *B01J 20/28052* (2013.01); *B01J 20/28057* (2013.01); *G01N 30/52* (2013.01); *G01N 30/6069* (2013.01); *B01J 2220/58* (2013.01); *G01N 30/6039* (2013.01); *G01N 2030/524* (2013.01)

(58) Field of Classification Search
CPC ............ B01J 20/28004; B01J 20/28016; B01J 20/282; B01J 20/286
See application file for complete search history.

(56) References Cited

U.S. PATENT DOCUMENTS

| | | | |
|---|---|---|---|
| 2007/0189944 A1 | 8/2007 | Kirkland et al. | |
| 2007/0295663 A1* | 12/2007 | Iraneta | G01N 30/603 210/656 |
| 2008/0272053 A1 | 11/2008 | Chandler | |

FOREIGN PATENT DOCUMENTS

| | | |
|---|---|---|
| GB | 2128099 A | 4/1984 |
| JP | 2001330598 | 11/2001 |
| WO | 9965586 A2 | 12/1999 |

OTHER PUBLICATIONS

Unger et al., "Particle packed columns and monolithic columns in high-performance liquid chromatography-comparison and critical appraisal," Journal of Chromatography A, 1184:393-415, 2008.

* cited by examiner

CHROMATOGRAPHY COLUMNS

CROSS REFERENCE TO RELATED APPLICATIONS

This application is a United States National Stage Application, under 35 U.S.C. §371, of International Application PCT/EP2013/069459, filed Sep. 19, 2013, entitled "IMPROVEMENTS IN AND RELATING TO CHROMATOGRAPHY COLUMNS," which claims the priority benefit to Great Britain Patent Application No. 1216984.3, filed Sep. 24, 2012, entitled "Improvements in and relating to chromatography columns" and to Great Britain Patent Application No. 1216985.0, filed Sep. 24, 2012, entitled "Improvements in and relating to chromatography columns," which applications are hereby incorporated herein by reference in their entireties.

FIELD OF THE INVENTION

This invention relates to the field of liquid chromatography.

BACKGROUND OF THE INVENTION

Liquid chromatography (LC) columns have been extensively developed and are used routinely in both analytical and preparative chromatography. The separation in a liquid chromatography column of a sample comprising a mixture of components is achieved by conveying the sample in a liquid mobile phase through a stationary phase, thereby causing the sample to separate into its components due to different partitioning between the mobile and stationary phases of each of the components (i.e. the components have different partition coefficients). In liquid chromatography the stationary phase is typically in the form of a bed of particles packed within the column, which is usually a tubular column. This invention relates to such so-called packed columns wherein the column media comprises packed particles.

Silica particles are commonly used as the stationary phase bed although other materials may be used. Non-porous particles have a low sample capacity. Therefore, porous particles are commonly used which contain a network of pores to increase the surface area of the stationary phase and thus improve the capacity of the separation. Larger porous particles tend to have longer mass transfer distances for the sample, which leads to slower separation and broader retention time peaks than with smaller porous particles. Consequently, there has been a trend to reduce the size of the porous particles in order to improve the kinetics and resolution of the separation. This is important for separation of large biomolecules, such as proteins for example. However, a consequence of using smaller porous particles is an increased resistance to flow and therefore a higher operating pressure is needed in order to deliver the required flow. Higher pressures increase the cost and complexity of the instrumentation.

An alternative to the aforementioned fully porous particles, in which the pores extend throughout the bulk of the particles, has been the use of so-called fused core particles, which are also sometimes termed superficially porous particles. These are particles that have a non-porous core (also termed a fused or solid core) and are only porous in an outer layer or region (also termed a shell) that surrounds the core, i.e. they are only porous at the surface, not throughout the bulk of the particles. These particles have some of the advantages of small porous particles, such as short mass transfer distances provided by the outer porous shell and hence high chromatographic efficiency, but the overall particle size is larger due to the solid core to enable lower operating pressures to be used. Fused core particles also offer the possibility of having narrower particle size distributions than porous particles due to the ability to classify larger, heavier particles more effectively.

Although the use of fused core particles has improved the column efficiency that can be delivered with lower pressures, there nevertheless remains a need to reduce still further the operating pressure whilst maintaining good column efficiency.

Against this background the present invention has been made.

SUMMARY OF THE INVENTION

According to an aspect of the present invention there is provided a chromatography column containing a bed of packed particles, wherein the packed particles comprise fused core particles and the particle diameters of the packed particles vary along the column.

According to another aspect of the present invention there is provided a method of chromatography comprising flowing a mobile phase containing a sample to be separated through a chromatography column containing a bed of packed particles wherein the packed particles comprise fused core particles and the particle diameters of the packed particles vary along the column.

Preferably, the particles of the bed are arranged in the column according to their particle diameter, as described in further detail below, most preferably in order of increasing particle diameter from the inlet end to the outlet end. The bed of particles may comprise a plurality of bed sections as described in further detail below. In such embodiments, preferably at least one bed section, more preferably each bed section, has a different average particle diameter (calculated from the particles in that section) to the other bed section(s). The bed sections with different particle diameters are preferably arranged in order of increasing particle diameter from the inlet to the outlet of the column. The smaller particles have a larger surface area per unit volume than bigger particles so that loading a sample onto smaller particles at the inlet end of the column requires a lower column volume and therefore the sample plug size is reduced. The rest of the particles in the column then act upon this small sample plug and column efficiency is maintained. Conversely, if a random mixture of particle sizes were used, then loading a sample onto the particles would require a larger column volume and therefore the sample plug size would be greater. The rest of the particles in the column would then act upon this broader sample plug.

According to still another aspect of the present invention there is provided a chromatography column, the column containing a bed of packed particles comprising fused core particles, wherein the bed comprises a plurality of bed sections and each bed section has an average particle diameter calculated from the particles in that section and there are at least two different average particle diameter bed sections, wherein the particles of each bed are separated from particles of an adjacent bed by a partition that is liquid permeable to allow through a flow of mobile phase. The partition substantially prevents particles from one section from mixing with particles of an adjacent section. Preferably, each bed section has a different average particle diameter to the other section(s).

Preferably, the bed sections are arranged according to their average particle diameter, most preferably in order of increasing average particle diameter from the inlet end to the outlet end. Thus, most preferably, the bed section with smallest particle diameter is arranged at the inlet end and the bed section with largest particle diameter is arranged at the outlet end, with any further bed sections preferably arranged in-between in order of increasing particle diameter going from the inlet to the outlet.

In certain preferred embodiments of the invention, the plurality of bed sections are arranged in a plurality of separate compartments in the column, i.e. each of the bed section is arranged in a separate compartment of the column. In a preferred embodiment, the column comprises a plurality of sub-columns, which are connectable together in series. When connected together, the series of sub-columns, which are relatively short, provide the column, which is relatively long. The bed sections thus may each be provided in a respective sub-column. Screw fittings, as well as push fittings, are typically connections between the sub-columns. Using a sub-column assembly configuration, the bed sections may each be prepared with packed particles of a desired diameter separately and independently from other bed section(s). The bed sections can be subsequently connected in series by connecting the sub-columns in series. The sub-columns may be of the same length, or one or more sub-columns may be of different length to the other(s).

The bed sections (and thus compartments, or sub-columns, containing the bed sections) are positioned in series along the length of the column, i.e. so that mobile phase flows through a first bed section, then through a second bed section and then optionally through any further bed section or sections. The bed sections are self contained so that particles of one bed section cannot mix with particles of an adjacent bed section, thereby separating the bed sections. A physical restriction (partition) is used to keep adjacent bed sections separate and improve the stability of the column bed. The use of a liquid-porous partition or barrier as a physical restriction between adjacent bed sections is a means for ensuring the self containment of the bed sections (i.e. a partition that allows passage of liquid but not the packed particles). A frit (i.e. a porous frit) is a suitable partition for this purpose, such as a steel frit. Other partitions could be a porous mesh, or a porous monolith, or a porous filter.

The number of bed sections (and thus compartments, or sub-columns, containing the bed sections) may be any suitable number of 2 or more, preferably 3 or more. For example 2, 3, 4, 5, 6, 7, 8, 9 or 10 beds may be employed. However, the invention is not limited to such specific embodiments and higher numbers of compartments could be used. The bed sections may be of equal or unequal length. In some embodiments, at least some of the bed sections are of different length to each other.

Each compartment may be provided as a separate partitioned section of a single column, i.e. each bed section may be provided in a separate partitioned section of a single column. Preferably, however, each compartment is provided as a separate column part (sub-column), i.e. each bed section is provided in a separate column part (sub-column), and the column parts (sub-columns) are connected together in series. Each column part (sub-column) may connect to an adjacent part (sub-column), preferably by a screw fit, or by a push fit.

The term fused core particle herein means a superficially porous particle in which a substantially non-porous core is surrounded by a porous outer region or shell.

Preferably, the packed particles are arranged with a gradient of particle diameters along the column. Especially, it is preferred to have a gradient of particle diameters wherein the particle diameters increase from the inlet end of the column to the outlet end of the column.

The particle diameters may vary along the column in a smooth gradient or in a stepwise gradient. A smooth gradient may be a constant gradient (i.e. same gradient) along the column, or a non-constant gradient (i.e. with different gradients) along the column. The gradient of particle diameters is most preferably positive (i.e. with particle diameters increasing) on going from the inlet end to the outlet end. A stepwise gradient may comprise any number, n, of step changes in the particle diameter along the column where n is an integer value of one or greater. The simplest embodiment therefore may be seen having one step change in particle diameter along the column, for example having a first grade of particles being of small diameter located closest to the inlet end of the column and a second grade of particles being of large diameter located closest to the outlet end of the column. In this context, the terms small and large refer to diameters of the particles relative to each other.

The particle diameter that varies with distance along the length of the column refers to the total, i.e. external, diameter of the particle. It refers to an average of particle diameters contained in a cross section through the column at a given distance along the column.

In some embodiments, additionally to the fused core particles a proportion of the packed particles may comprise fully porous particles. In such embodiments, the proportion of the packed particles that are fully porous particles is preferably a minor proportion. Desirably, where present, such fully porous particles are packed at the inlet end of the column, for example closer to the inlet than the first or smallest fused core particles. The fully porous particles furthermore are desirably of small diameter, typically being of the smallest particle diameter of the packed particles. However, preferably the packed particles substantially comprise, or more preferably completely consist of, fused core particles.

The outer porous layer thickness of the fused core particles preferably should be at least 5% but more preferably at least 10% of the solid core diameter. For example, if the core is 1 μm in diameter then the thickness of the porous layer should be ideally at least 0.1 μm (i.e. 10%) and if the core is 3 μm in diameter then the thickness of the porous layer should be ideally at least 0.3 μm. The outer porous layer thickness should preferably be not more than 2 μm. The outer porous layer thickness is typically in the range 0.2 to 2 μm, for example in the range 0.2 to 1 μm.

Of beneficial use are fused core particles wherein the thickness of the outer porous layer is similar or substantially the same for all the particles. Thus, in such embodiments, whilst the particle diameter of the fused core particles varies with distance along the column, the thickness of the porous outer layer of the particles preferably does not substantially vary with distance along the column. Instead, in such embodiments, it is the diameter of the non-porous core of the fused core particles that varies with distance along the column to thereby vary the total diameter. Thus, in the embodiments with a bed comprising a plurality of bed sections, all the particles in all the bed sections have similar or substantially the same thickness of their outer porous layer. A substantially constant thickness of the outer porous layer of the particles along the column length maintains a uniform mass transfer distance for all of the packed particles. This maintains chromatographic efficiency and resolution in the column. However, some embodiments are possible in which along the column length from inlet to outlet the thickness of the outer porous layer may reduce, i.e. as the sample progresses through the column.

Preferably, the particle diameter of the packed particles varies with distance along the column such that smaller particles are packed at the inlet end of the column and larger particles are packed at the outlet end. Using smaller diameter particles at the inlet end means that there is maximum surface area per unit volume at the part of the column where the sample is loaded, which maintains the loadability of the column. Employing larger diameter particles at the outlet end means that the pressure of the flow can be reduced compared to a column with only small particles throughout the whole column.

The invention provides the advantage that high column efficiency can be provided with lower pressure drop per unit length of the column. This reduction in operating pressure has benefits in terms of reduced cost of the instrumentation. Moreover, longer columns may be used to give higher chromatography efficiency without excessive pressure needing to be applied to the flow. The loadability of the column is maintained by providing the smallest particles at the inlet end of the column. Larger particles, preferably at the outlet end, are used to reduce the pressure drop.

The bed of the column, or any one or more bed sections thereof, may comprise an amount of non-porous particles additionally to the fused core particles, which may reduce the dispersion of a sample as it passes through the column and improve peak sharpness. The amount of such non-porous particles is a minor amount relative to the amount of fused core particles typically.

Suitable fused core particles are available in commercial quantities and methods are known for their manufacture. For example, fused core particles are available commercially in High Performance Liquid Chromatography (HPLC) columns in Poroshell™ columns from Agilent and Accucore™ columns from Thermo Scientific.

In a known procedure described in U.S. Pat. No. 3,505,785, fused core silica particles are prepared via multilayer coatings of silica colloids on the surface of non-porous silica microspheres acting as solid cores. Between two and thirty layers of colloid particles are described in that method. Another method of preparing fused core silica is a coacervation method, described in J. J. Kirkland, F. A. Truszkowski, and C. H. Dilks Jr, G. S. Engel, *Journal of Chromatography A*, 890 (2000) 3-13, in which solid (i.e. non-porous) silica microspheres are coated by a coacervate of a polymer and silica sol, with the polymer being subsequently removed by heating at high temperature.

The preceding techniques use silica nanoparticles on the surface of silica microparticles as the basis for forming fused core particles. Another method, described in US 2010/0051877 A, involves the pseudomorphic transformation of the surface of silica microparticles. During the process, the outer layer of the core particle is dissolved and re-precipitates to form a porous layer on the surface.

Another technique for forming fused core particles is described in the applicant's patent application no. GB 1120665.3 filed on 1 Dec. 2011 (spheres on sphere particles).

The contents of the foregoing references describing methods of forming fused core particles are hereby incorporated in this application in their entirety.

In accordance with different methods existing for forming fused core particles, the fused core particles may have one of numerous different morphologies. For example, a fused core may be surrounded by one or more layers of much smaller particles, the layer or layers of smaller particles forming the porous outer layer (so-called spheres-on-sphere particles). For example, the non-porous core may be a microparticle (1 µm to 100 µm diameter, especially 1 µm to 10 µm) and the smaller particles may be nanoparticles (1 nm to 1000 nm). In other embodiments, the fused core particles may comprise a non-porous core that has a modified outer region that is porous.

The diameters of the fused core particles may range in their total (external) size from, for example, about 1 µm diameter to about 100 µm diameter, preferably from 1 µm to 10 µm. The particles may range in their external size along the column, for example, having particles in the range from about 1-3 µm (especially 1-2 µm) diameter at the inlet end to having particles in the range of 5-10 µm diameter at the outlet end. Numerous methods for measuring particle sizes an dimensions are known to the skilled person, for example electrozone sensing, or dynamic light scattering, or disk centrifugation, or image analysis, or electron microscopy. The particle sizes specified herein refer to sizes as measured by electrozone sensing. Preferably, the ratio of the largest particle size (e.g. at the outlet) to the smallest particle size (e.g. at the inlet) lies in the range from 20:1 to 2:1, more preferably in the range from 10:1 to 2:1. The porous outer layer thickness is preferably not greater than 2 µm, typically not greater than 1 µm, e.g. 10 nm to 1000 nm (1 µm).

The surface area of the particles at the inlet end is preferably in a range greater than 50 m$^2$/g, more preferably greater than 100 m$^2$/g. The surface area of the particles at the outlet end is preferably in a range less than 10 m$^2$/g.

A chromatography column in accordance with the present invention is for liquid chromatography and may be suitable for analytical or preparative chromatography. It may be suitable, for example, as an HPLC column (which term herein includes within its scope an Ultra HPLC (UHPLC) column). However, the column is not limited to such uses but may be employed in any setting in which it is desirable to maintain column efficiency but reduce operating pressure.

DESCRIPTION OF EMBODIMENTS OF THE INVENTION

In order to enable further understanding of the invention, but without limiting the scope thereof, various exemplary embodiments of the invention are now described with reference to the accompanying drawings.

Figure 1:
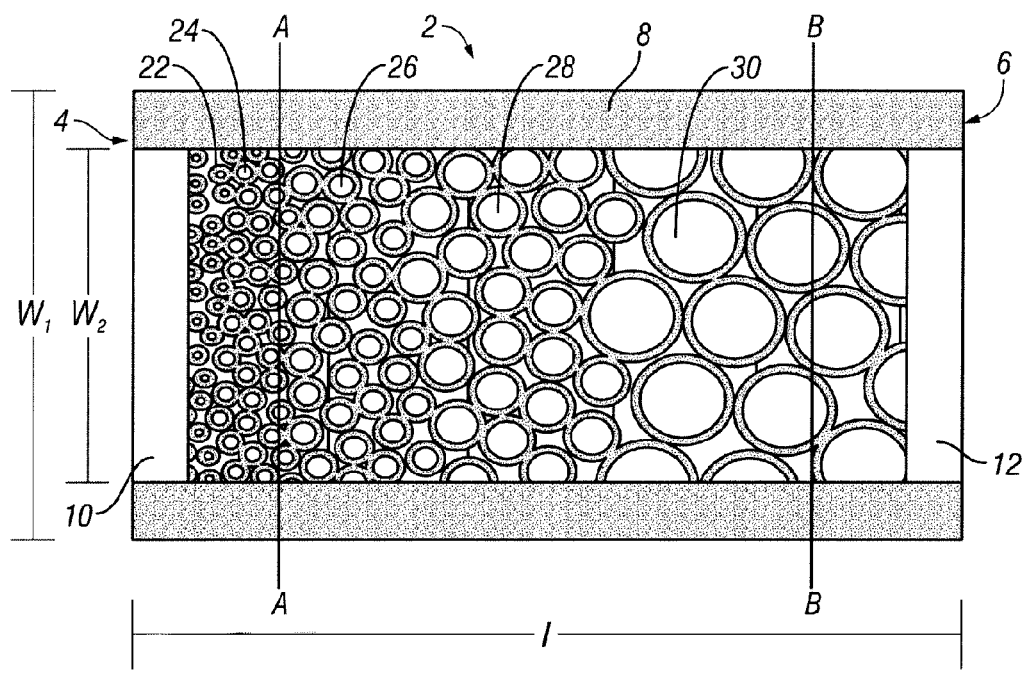
FIG. 1 shows a schematic arrangement of a chromatography column packed with a bed of fused core particles in accordance with the present invention.

Referring to FIG. 1, there is shown a schematic arrangement of a chromatography column (2) packed with a bed of particles in accordance with the present invention. The Figure shows a cross-sectional side view of the column, i.e. a section taken longitudinally along the length of the column. The column comprises a tube (8), commonly made of metal such as stainless steel for example. The column has a circular cross section in transverse cross section, orthogonal to the length e.g. in a section through line A-A or B-B. The column has a length, l, an outer tube diameter, w1, and an inner tube diameter, w2, as shown. The column may be an HPLC column made of steel and of circular section. However, it will be appreciated that column shapes, geometries and materials other than the example shown may be used, depending on the chromatographic application.

The column has an inlet end (4) and an outlet end (6). In use, a liquid mobile phase containing a sample to be separated into components is flowed through the packed column from the inlet end to the outlet end. The inlet end is plugged with a porous frit (10) for retaining the packed particles in the column but allowing through a liquid flow into the column. The outlet end is also plugged with a porous frit (12), similarly for retaining the packed particles in the column but allowing through the liquid outflow, e.g. to a detector.

Figure 2:
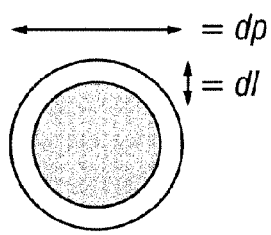
FIG. 2 shows schematically the structure of the fused core particles having an outer porous layer and solid core.

In known HPLC systems, a mobile phase is forced through a chromatography column under high pressure pumping due to the packing of small particles in the column in order to achieve high column efficiency, i.e. high chromatographic resolution. The column shown in FIG. 1 is packed with particles in accordance with the present invention to reduce the pressure in the column without compromising the column efficiency. The column is packed with fused core particles having a gradient of particle diameters, i.e. particles arranged in order of increasing particle diameter. The particles are silica particles, as is typically the case, but may be made of other materials in alternative embodiments. The fused core particles all have a similar outer porous layer thickness, di, and thereby mass transfer distance, but differ by their fused core diameter (and therefore their total diameter, $d_p$) as illustrated in FIG. 2. The smaller particles are packed at the inlet end of the column to ensure maximum surface area per unit volume at the inlet of the column where the sample is introduced, thereby maintaining an effective column loadability. The larger particles packed downstream act to reduce the pressure that is required to force the flow of mobile phase through the column. Thus, the particle diameter of the packed fused core particles increases as the sample travels through the column bed from the inlet towards the outlet. The column bed can thus be seen to comprise a plurality of bed sections, which contain different sizes of particles.

In the embodiment shown, at the inlet end, an amount of the smallest fused core particles (22) are arranged against the inlet frit (10) and packed adjacent to the smallest particles are an amount of slightly larger fused core particles (24). The slightly larger particles (24), however, have the same outer porous layer thickness as the smallest particles (22). The next size of fused core particles (26) are larger still than the particles (24) and an amount of them is packed against the particles (24). An amount of even larger fused core particles (28), larger than the particles (26), is packed against the particles (26). At the outlet end, packed against the particles (28) is an amount of the largest sized particles (30), which is arranged against the outlet frit (12). Thus, in this embodiment, there are five different grades of particle diameters (22), (24), (26), (28) and (30) arranged from the inlet in order of increasing diameter. In other embodiments, there may be fewer or more than five different grades of particle diameters. It is, however, preferable to have at least one particle size in between the smallest size at the inlet and the largest size at the outlet. In an exemplary embodiment, the particle size diameters of the particle grades (22), (24), (26), (28) and (30) are as follows. Grade (22) has an average particle diameter of 1.9 µm, grade (24) has an average particle diameter of 2.7 µm, grade (26) has an average particle diameter of 3.0 µm, grade (28) has an average particle diameter of 5.0 µm, and grade (30) has an average particle diameter of 8.0 µm. The column shown is suitable for HPLC, more specifically UHPLC.

In an optional variation on the embodiment shown in FIG. 1, in addition to fused core particles, there may also be used an amount of fully porous particles. Preferably, the fully porous particles are of the smallest diameter of the fused particles or smaller still, and are arranged at the inlet end. More preferably, the fully porous particles are to be the particles first encountered by the mobile phase as it enters the column.

Figure 3:
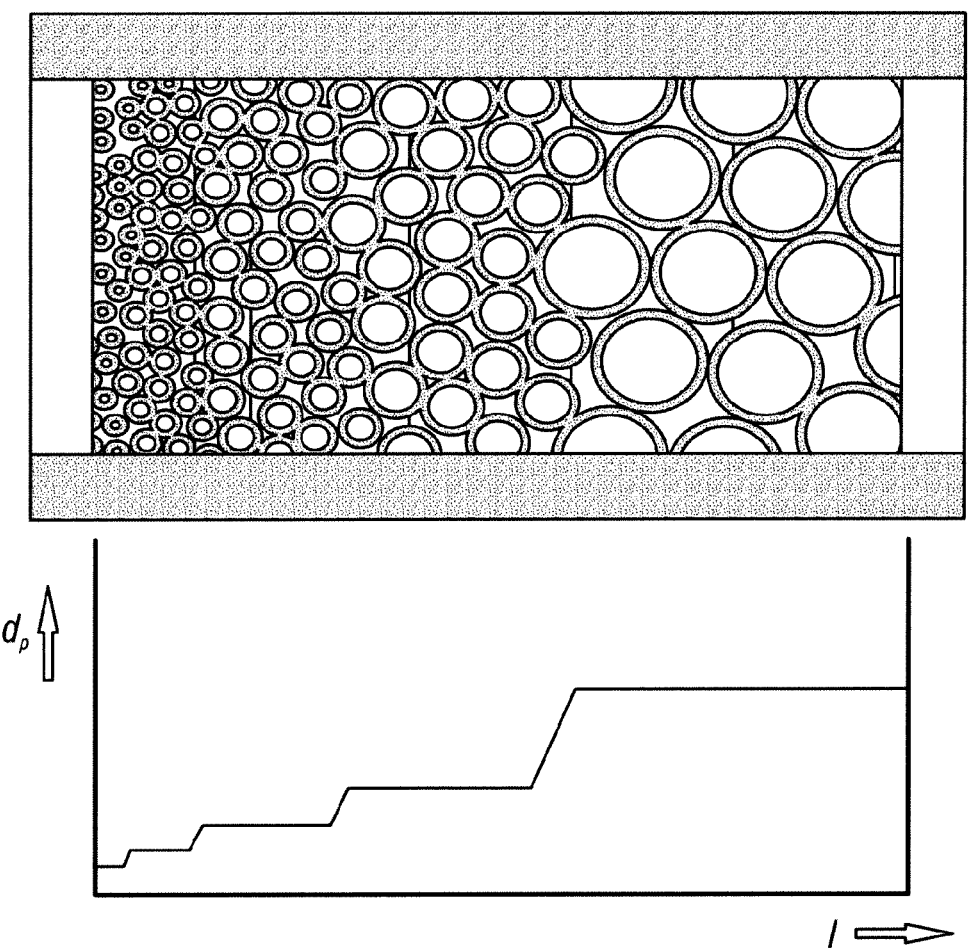
FIG. 3 shows schematically the particle diameter gradient of the FIG. 1 embodiment.
Figure 4A:
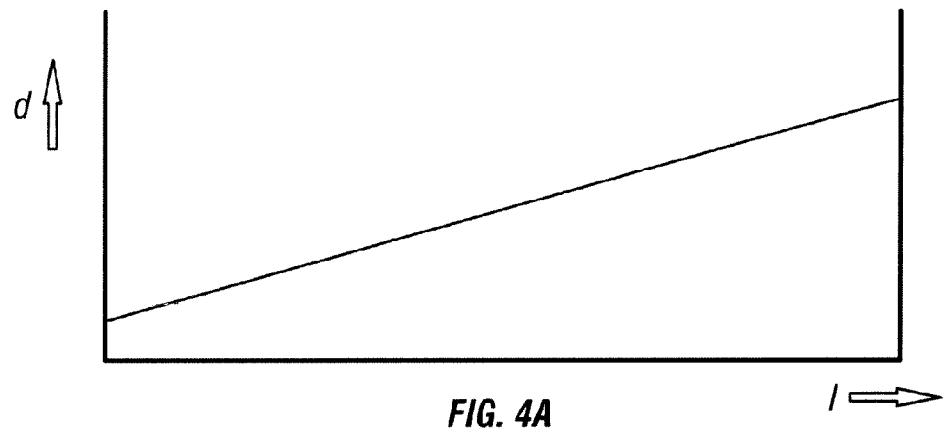
FIG. 4 shows schematically various other exemplary particle size gradients that could be employed in the invention.
Figure 4B:
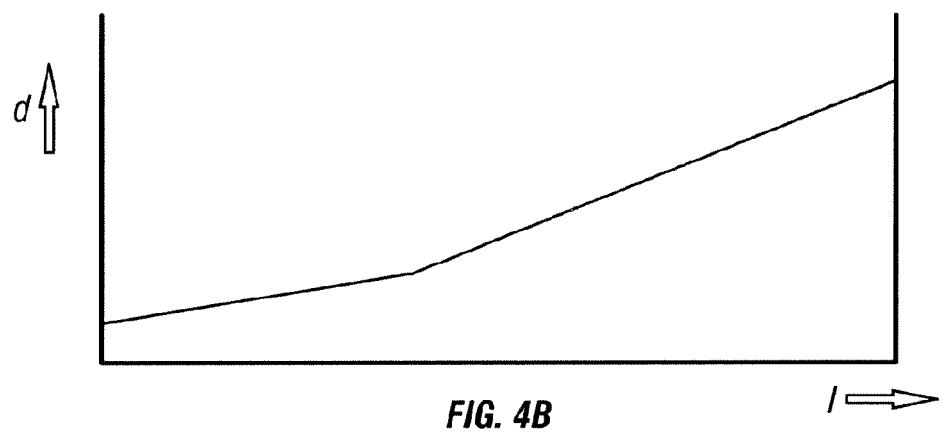
Figure 4C:
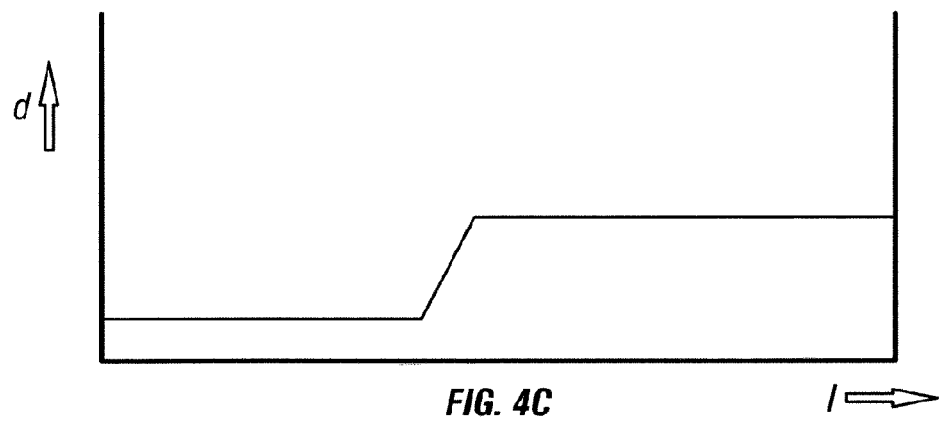

Referring to FIG. 3, there is shown schematically the particle diameter gradient of the FIG. 1 column embodiment, i.e. showing the average particle diameter, $d_p$, of particles in a transverse cross section of the column as it varies along the length of the column, l. The step change in particle diameter is seen at the transition from one grade of particle size to another, FIG. 4 shows schematically various other exemplary particle size gradients that could be employed. Plot A schematically represents an embodiment having a constant gradient of particle diameter, plot B schematically represents an embodiment having a non-constant gradient of particle diameter, i.e. with a change in the gradient, and plot C schematically represents an embodiment having a step change in a simple case of two grades of particle sizes.

Figure 5:
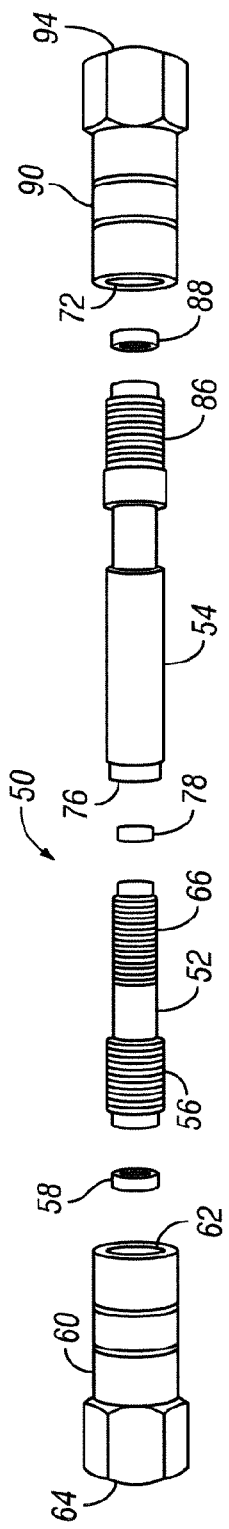
FIG. 5 shows schematically an exploded view of a disassembled UHPLC column in accordance with the present invention for containing multiple column bed sections of different particle size.
Figure 6:
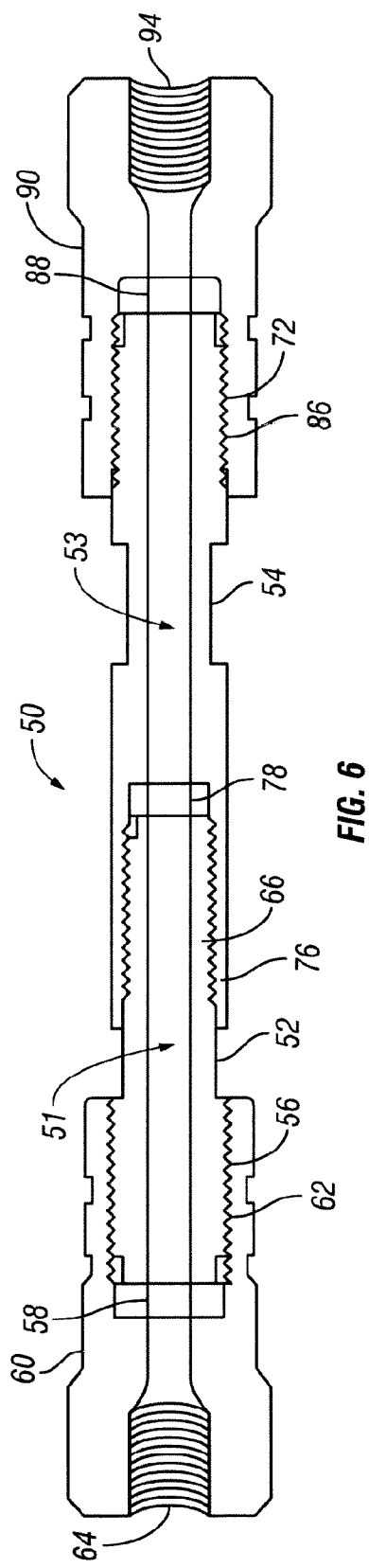
FIG. 6 shows schematically a longitudinal cross section of the column of FIG. 5 in an assembled state.

The stability of the column bed may be improved by the use of physical means for keeping the column bed sections of different particle sizes separate. Referring to FIG. 5, there is shown an exploded view of a disassembled UHPLC column (50) for containing multiple (in this case two) bed sections of different particle size. Referring to FIG. 6, there is shown a longitudinal cross section of the column (50) in an assembled state. The column (50) comprises a first sub-column (52) that in use contains a first bed section (51) therein that comprises fused core particles, generally all of a small particle diameter (relative to the particles in a second bed section as hereafter described). The column (50) also comprises a second sub-column (54) that in use contains a second bed section (53) therein that comprises fused core particles, generally all of a large particle diameter (relative to the grades in the first bed section). The fused core particles in both sub-columns have substantially the same outer porous layer thickness. The first sub-column is assembled at the inlet side of the column and the second sub-column is assembled at the outlet side. The first and second sub-columns (52) and (54) are each provided as a ¼ inch fitting having a 2.1 mm×25 mm column (diameter× length).

The column (50) is assembled in the following manner. The first sub-column piece (52) carries a male (external) screw thread (56) at its inlet end. The inlet end of the first sub-column (and hence the overall column) is closed by a liquid porous inlet frit (58), which fits inside a standard UHPLC (¼ inch) end fitting (60). The frit (58) is a stainless steel collared frit. The male thread (56) of the first sub-column piece screws into a female (internal) thread (62) inside the end fitting (60) until the inlet frit (58) is tight between the end of the first sub-column (52), and the end fitting (60). The end fitting (60) is connected to tubing (not shown) via its other end (64) that in use conveys a pumped supply of mobile phase into the column.

The other end of the first sub-column (52) carries another male thread (66), which screws into a female thread (76) in one end of the second sub-column (54). Thereby, the first and second sub-columns may be connected together. The packed particle beds of the two sub-columns are kept separate and thus stability is provided to the column bed by means of a liquid-porous frit (78), which fits between the two sub-columns and thus between the two bed sections (51), (53). The frit (78) is a 0.5 micron PEEK collared frit. The male thread (66) of the first sub-column piece screws into the female thread (76) inside the second sub-column until the frit (78) is tight between the first and second sub-columns (52).

The other, outlet end of the second sub-column (54) carries a male screw thread (86). The outlet end is closed by a liquid porous outlet frit (88), which fits inside a standard UHPLC end fitting (¼ inch) (90). The frit (88) is a stainless steel collared frit, identical to the inlet frit (58). The male thread (86) of the second sub-column piece screws into a female (internal) thread (72) inside the end fitting (90) until the outlet frit (88) is tight between the end of the second sub-column (54) and the end fitting (90). The end fitting (90) is connected to tubing (not shown) via its other end (94) that conveys the eluate from the column to a detection system (not shown).

This embodiment can be seen to connect together the sub-columns (52), (54) by a low dead volume system (male/female fitting, containing a frit). It enables the two beds (51) and (53) of respectively smaller and larger size fused core particles (with the same outer porous layer thickness) to be conveniently prepared and arranged in their own respective sub-column (52) and (54), with physical separation of the beds being provided by a porous barrier in the form of a frit (78). A stable bed is thereby provided with a gradient of particle sizes.

Figure 7:
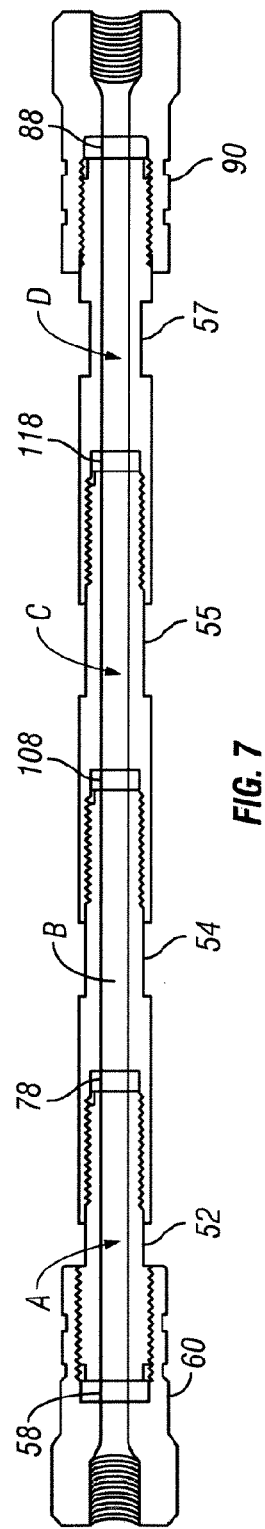
FIG. 7 shows schematically an embodiment according to the invention comprising four column bed sections contained in four sub-columns.

In other embodiments, there may be more than two sub-columns as shown, for example, in FIG. 7. In that embodiment, a sub-column (52) is provided in the manner shown in FIG. 6, being connected to end fitting (60) and connected at its other end to second sub-column (54) as before (like parts are denoted by the same reference numerals). However, whereas in the FIG. 6 embodiment the second sub-column (54) is connected at its other end to another end fitting (90), in the FIG. 7 embodiment the second sub-column (54) is connected to a third sub-column (55), which is of the same construction as the second sub-column (54). That is, the male thread of the second sub-column (54) connects to the female thread of the third sub-column (55). The third sub-column (55) in turn is connected to a fourth sub-column (57), which is also of the same construction as the second sub-column (54) and third sub-column (55). That is, the male thread of the third sub-column (55) connects to the female thread of the fourth sub-column (57). Finally, the fourth sub-column (57) is connected to the end fitting (90), i.e. the male thread of the fourth sub-column (57) connects to the female thread of the end fitting (90). In other embodiments, more than four sub-columns may be used.

The use of four sub-columns as shown in FIG. 7 enables four bed sections of different particle size to be employed. The first sub-column (52) in use contains a first bed section A that comprises fused core particles, generally all of the smallest particle diameter (relative to the other bed sections). The second sub-column (54) in use contains a second bed section B that comprises fused core particles, generally all of a larger particle diameter (relative to the particle size grades in the first bed section A). The third sub-column (55) in use contains a third bed section C that again comprises fused core particles, generally all of a larger particle diameter still (larger relative to the particle size grades in the second bed section B). Finally, the fourth sub-column (57) in use contains a fourth bed section D that once again comprises fused core particles, generally all of the largest particle diameter (larger than the particle size grades in the third bed section C). In other words, the average particle diameter, $d_p$, of A<B<C<D. Whilst the fused core particles in the different bed sections differ in their external particle diameter, $d_p$, the fused core particles in all four sub-columns have substantially the same outer porous layer thickness ($d_l$), i.e. di of A~B~C~D. As before, the sub-columns (and hence the bed sections that they contain) are partitioned from each adjacent sub-column (bed section) by means of frits inside each of the screw fittings. The first sub-column (52) and second sub-column (54) are partitioned by the frit (78) as before, the second and third sub-columns are partitioned by a frit (108) and the third and fourth sub-columns are partitioned by a frit (118). The partitioning with the frits provides stability to the multi-section bed arrangement.

Figure 8:
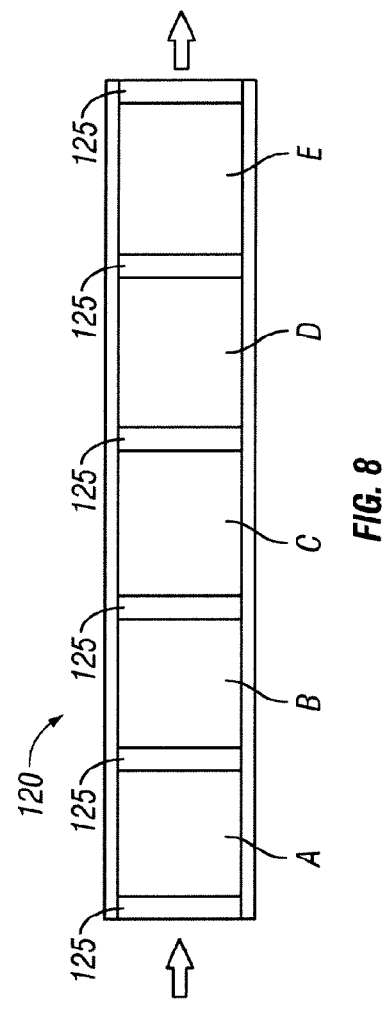
FIG. 8 shows a further embodiment according to the present invention.

Alternative to the modular, sub-column construction shown in FIGS. 5 to 7, in other embodiments, a single column 120 could be packed with particles of multiple size grades with a partition, such as a frit, 125, located between adjacent particle size grades, as shown in FIG. 8, where A, B, C, D and E indicate beds of different size grades of fused core particles, all with approximately the same outer porous layer thickness (i.e. $d_l$ of A~B~C~D~E), where the particle diameter, $d_p$, of A<B<C<D<E and the mobile phase flows in the direction indicated by the arrows.

Table 1 below shows data for a uniform size bed representing how the particle diameter, $d_p$, (μm) of the bed media of a column affects both the pressure drop (ΔP, bar) for HPLC and the corresponding column efficiency (number of theoretical plates, N) for a 100 mm length column. Table 1 shows that decreasing the particle diameter increases the column efficiency (higher N) but with greatly increased pressure required. For example, with 8 μm particles a chromatographic separation with an N value of 5000 is achieved with a pressure drop of 50 bar, whereas with 1.9 μm particles a separation with an N value of 22000 is achieved but with a much higher pressure drop of 520 bar (higher applied pressure needed). The present invention seeks to address the problem of requiring such higher pressures. For the particles referred to in Table 1 and Table 2, the porous layer thickness is 0.35 μm for the 1.9 um particles, which have a 1.2 μm diameter core (i.e. 0.35+1.2+0.35=1.9 μm). For 8 μm particles and all others, the porous layer is 0.5 μm, for example (0.5+7.0+0.5)=8 μm etc.

Table 2 shows data giving the pressure drop (ΔP) and column efficiency in terms of the number of plates (N) for a 100 mm (i.e. 10 cm) length column, for several different cases where the 10 cm column length is made up of a plurality of particle beds having different particle size profiles. The second to sixth columns of the Table indicate the number of centimeters (cm) of the 10 cm column length that are comprised by the various different particle size grades: 1.9 μm, 2.7 μm, 3 μm, 5 μm and 8 μm. Thus, the rows of the Table represent different columns packed with different combinations of particles from these five grades of particle size. Where multiple size grades were used, the grades were arranged in the column in ascending size order, i.e. with the smallest size grade placed at the inlet. The seventh and eight columns of the Table give the pressure drop (ΔP) and the number of theoretical plates (N) respectively for each of the different column compositions. The ninth and tenth columns of the Table respectively indicate the pressure drop (ΔP) and number of plates (N) for each composition as a % change relative to the values for the column comprising solely the smallest particles (1.9 μm), i.e. where all 10 cm of the column comprises the 1.9 μm particles. The final column indicates the % ratio of the relative % change in N to the relative % change in ΔP, % N/% ΔP.

From Table 2 it can be seen that, compared to the case of a column comprising solely the smallest, 1.9 μm particles, columns having a small amount of the smallest (1.9 μm) particles at the inlet and larger particles packed further downstream in the column, arranged in a gradient of multiple particle sizes from inlet to outlet, can still achieve a high N value but with a much smaller pressure drop across the column (therefore less applied pressure required). For example, compared to the purely 1.9 μm 10 cm column, a column with 2 cm column length of 1.9 μm particles at the inlet followed by 2 cm column length of each of the other sizes of particles yields 80% of the column efficiency N for only 46% of the pressure drop (ΔP), giving a % N/% ΔP ratio of 173%.

TABLE 1

| $d_p$ (μm) | ΔP (bar) for 100 mm | N for 100 mm |
|---|---|---|
| 1.9 | 520 | 22000 |
| 2.7 | 320 | 18000 |
| 3 | 200 | 12000 |
| 5 | 110 | 9000 |
| 8 | 50 | 5000 |

TABLE 2

| | $d_p$ (μm) | | | | | ΔP (bar) | N for Bed | % of 1.9 ΔP | % of 1.9 N | % N/% ΔP |
|---|---|---|---|---|---|---|---|---|---|---|
| | 1.9 | 2.7 | 3 | 5 | 8 | | | | | |
| cm of Bed | 10 | 0 | 0 | 0 | 0 | 520 | 22,000 | 100% | 100% | 100% |
| cm of Bed | 2 | 8 | 0 | 0 | 0 | 360 | 20,400 | 69% | 93% | 134% |
| cm of Bed | 2 | 0 | 8 | 0 | 0 | 264 | 18,800 | 51% | 85% | 168% |
| cm of Bed | 2 | 2 | 2 | 2 | 2 | 240 | 17,600 | 46% | 80% | 173% |
| cm of Bed | 1 | 2 | 2 | 2 | 3 | 193 | 16,600 | 37% | 75% | 203% |
| cm of Bed | 1 | 1 | 2 | 3 | 3 | 172 | 16,200 | 33% | 74% | 223% |

As used herein, including in the claims, unless the context indicates otherwise, singular forms of the terms herein are to be construed as including the plural form and vice versa. For instance, unless the context indicates otherwise, a singular reference, such as "a" or "an" means "one or more".

Throughout the description and claims of this specification, the words "comprise", "including", "having" and "contain" and variations of the words, for example "comprising" and "comprises" etc, mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example", "e.g." and like language) provided herein, is intended merely to better illustrate the invention and does not indicate a limitation on the scope of the invention unless otherwise claimed. No language in the specification should be construed as indicating any non-claimed element as essential to the practice of the invention.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

The invention claimed is:

1. A chromatography column comprising a bed of packed particles, wherein the packed particles include fused core particles and the particles of the bed are arranged in the column according to their particle diameter, wherein the outlet end of the chromatography column is plugged with a porous frit configured to retain the packed particles in the chromatography column but allowing through a liquid outflow,
   wherein the bed of particles comprises a plurality of bed sections and at least one bed section has a different average particle diameter calculated from the particles in that bed section to the other bed section(s),
   wherein the plurality of bed sections are arranged in a plurality of separate compartments in the column, and
   wherein the bed sections are arranged according to their average particle diameter in order of increasing average particle diameter from the inlet end to the outlet end of the column.

2. The chromatography column as claimed in claim 1, wherein the thickness of an outer porous layer of the fused core particles is substantially the same for all the particles.

3. The chromatography column as claimed in claim 1, wherein the plurality of bed sections are arranged in series along the length of the column.

4. The chromatography column as claimed in claim 3, wherein the number of bed sections is from 3 to 10.

5. The chromatography column as claimed in claim 4, wherein the particles of each bed section are separated from particles of an adjacent bed section by a partition that is liquid permeable to allow through a flow of mobile phase.

6. The chromatography column as claimed in claim 5, wherein each partition substantially prevents particles from one section from mixing with particles of an adjacent section.

7. The chromatography column as claimed in claim 5, wherein the partition is a frit.

8. The chromatography column as claimed in claim 1, wherein each bed section comprises a different size grade of particles to form a gradient.

9. The chromatography column as claimed in claim 1, wherein at least some of the bed sections are of different length.

10. The chromatography column as claimed in claim 1, wherein the particle diameters vary along the column according to a stepwise gradient.

11. The chromatography column as claimed in claim 1 wherein additionally to the fused core particles a minor proportion of the packed particles comprise fully porous particles.

12. A chromatography column, comprising a bed of packed particles, wherein the packed particles include fused core particles and the particles of the bed are arranged in the column according to their particle diameter, wherein the outlet end of the chromatography column is plugged with a porous frit configured to retain the packed particles in the chromatography column but allowing through a liquid outflow,
wherein the bed of particles comprises a plurality of bed sections and at least one bed section has a different average particle diameter calculated from the particles in that bed section to the other bed section(s),
wherein the column comprises a plurality of sub-columns that are connectable together in series, wherein the bed sections are each provided in a respective sub-column, and
wherein the bed sections are arranged according to their average particle diameter in order of increasing average particle diameter from the inlet end to the outlet end of the column.

13. The chromatography column as claimed in claim 12, wherein the sub-columns are connectable together by screw fittings.

14. The chromatography column as claimed in claim 13, wherein a partition is located in the screw fitting between sub-columns, in which the partition is liquid permeable to allow through a flow of mobile phase.

15. The chromatography column as claimed in claim 12, wherein the thickness of an outer porous layer of the fused core particles is substantially the same for all the particles.

16. The chromatography column as claimed in claim 12, wherein each bed section comprises a different size grade of particles to form a gradient.

17. The chromatography column as claimed in claim 12, wherein at least some of the bed sections are of different length.

18. The chromatography column as claimed in claim 12, wherein the particle diameters vary along the column according to a stepwise gradient.

19. The chromatography column as claimed in claim 12, wherein additionally to the fused core particles a minor proportion of the packed particles comprise fully porous particles.

20. A chromatography column, comprising a bed of packed particles, wherein the packed particles include fused core particles and the particles of the bed are arranged in the column according to their particle diameter, wherein the outlet end of the chromatography column is plugged with a porous frit configured to retain the packed particles in the chromatography column but allowing through a liquid outflow,
wherein the bed of particles comprises a plurality of bed sections and at least one bed section has a different average particle diameter calculated from the particles in that bed section to the other bed section(s),
wherein the bed sections are of equal length, and
wherein the bed sections are arranged according to their average particle diameter in order of increasing average particle diameter from the inlet end to the outlet end of the column.

21. A method of chromatography comprising flowing a mobile phase containing a sample to be separated through a chromatography column, the chromatography column comprising:
a bed of packed particles, wherein the packed particles include fused core particles and the particles of the bed are arranged in the column according to their particle diameter, wherein the outlet end of the chromatography column is plugged with a porous frit configured to retain the packed particles in the chromatography column but allowing through a liquid outflow,
wherein the bed of particles comprises a plurality of bed sections and at least one bed section has a different average particle diameter calculated from the particles in that bed section to the other bed section(s),
wherein the plurality of bed sections are arranged in a plurality of separate compartments in the column, and
wherein the bed sections are arranged according to their average particle diameter in order of increasing average particle diameter from the inlet end to the outlet end of the column.

* * * * *